(12) United States Patent
Zdenek et al.

(10) Patent No.: US 6,991,650 B2
(45) Date of Patent: Jan. 31, 2006

(54) SCLERAL EXPANSION DEVICE HAVING DUCK BILL

(75) Inventors: Gene W. Zdenek, West Hills, CA (US); Ronald A. Schachar, Dallas, TX (US)

(73) Assignee: ReFocus Ocular, Inc., Dallas, TX (US)

( * ) Notice: Subject to any disclaimer, the term of this patent is extended or adjusted under 35 U.S.C. 154(b) by 339 days.

(21) Appl. No.: 09/863,006

(22) Filed: May 22, 2001

(65) Prior Publication Data

US 2002/0002403 A1 Jan. 3, 2002

Related U.S. Application Data

(63) Continuation-in-part of application No. 09/061,168, filed on Apr. 16, 1998, now Pat. No. 6,280,468, which is a continuation-in-part of application No. 08/946,975, filed on Oct. 8, 1997, now Pat. No. 6,007,578, application No. 09/863,006, which is a continuation-in-part of application No. 09/472,535, filed on Dec. 29, 1999, now Pat. No. 6,299,640, which is a continuation of application No. 08/946,975, application No. 09/863,006, which is a continuation-in-part of application No. 09/589,626, filed on Jun. 7, 2000, which is a continuation-in-part of application No. 09/472,535, and a continuation-in-part of application No. 09/061,168, and a continuation-in-part of application No. 08/946,975, application No. 09/863,006.

(60) Provisional application No. 60/206,134, filed on May 22, 2000.

(51) Int. Cl.
*A61F 2/14* (2006.01)

(52) U.S. Cl. ...................................................... 623/4.1

(58) Field of Classification Search ................. 623/4.1, 623/11.11, 905; 606/204.25
See application file for complete search history.

(56) References Cited

U.S. PATENT DOCUMENTS

| 2,952,023 A | 9/1960 | Rosen ............................ 3/13 |
| 3,064,643 A | 11/1962 | Dixon ....................... 128/76.5 |
| 3,454,966 A | 7/1969 | Rosen ............................ 3/13 |

(Continued)

FOREIGN PATENT DOCUMENTS

| FR | 2 784 287 | 10/1998 |
| FR | 2 791 552 | 6/2000 |
| WO | WO 94/18921 | 9/1994 |

(Continued)

OTHER PUBLICATIONS

Schachar, "Cause and Treatment of Presbyopia With a Method for Increasing the Amplitude of Accomodation," Ann Ophthalmol, 24: 445–452 (1992).

(Continued)

*Primary Examiner*—Corrine McDermott
*Assistant Examiner*—William H. Matthews

(57) ABSTRACT

A prosthesis for scleral expansion includes a central body portion and at least one end portion having a width greater than the width of the central body portion. The end portion therefore inhibits rotation of the prosthesis about a long axis when the prosthesis is implanted within a scleral pocket or tunnel. The other end of the central body portion may have a blunted end portion including grooves for receiving a edge or lip of an incision forming the scleral tunnel to inhibit the prosthesis from sliding within the scleral tunnel. Curvature of the bottom surface of the central body portion may be greater than the curvature of the innermost surface of the scleral tunnel so that contact between the scleral and the bottom surface of the prosthesis is primarily with the end portions.

7 Claims, 10 Drawing Sheets

U.S. PATENT DOCUMENTS

| | | | |
|---|---|---|---|
| 4,439,198 A | 3/1984 | Brightman, II et al. | |
| 4,521,210 A | 6/1985 | Wong | 604/8 |
| 4,549,529 A | 10/1985 | White | |
| 4,863,457 A | 9/1989 | Lee | |
| 4,946,436 A | 8/1990 | Smith | 604/8 |
| 4,976,719 A | 12/1990 | Siepser | 606/151 |
| 5,354,331 A | 10/1994 | Schachar | 623/4 |
| 5,370,607 A * | 12/1994 | Memmen | 604/8 |
| 5,443,505 A | 8/1995 | Wong et al. | |
| 5,465,737 A | 11/1995 | Schachar | |
| 5,489,299 A | 2/1996 | Schachar | |
| 5,503,165 A | 4/1996 | Schachar | |
| 5,520,631 A | 5/1996 | Nordquist et al. | 604/8 |
| 5,529,076 A | 6/1996 | Schachar | |
| 5,558,630 A | 9/1996 | Fisher | 604/8 |
| RE35,390 E | 12/1996 | Smith | 604/8 |
| 5,707,643 A | 1/1998 | Ogura et al. | |
| 5,722,952 A | 3/1998 | Schachar | |
| 5,731,909 A | 3/1998 | Schachar | |
| 5,766,242 A | 6/1998 | Wong et al. | 623/4 |
| 5,774,274 A | 6/1998 | Schachar | |
| 5,824,086 A | 10/1998 | Silverstrini | |
| RE35,974 E | 12/1998 | Davenport et al. | |
| 5,846,256 A | 12/1998 | Mathis et al. | |
| 5,855,604 A | 1/1999 | Lee | |
| 5,879,319 A | 3/1999 | Pynson et al. | 604/8 |
| 5,888,243 A | 3/1999 | Silverstrini | |
| 5,919,228 A | 7/1999 | Hennig | |
| 5,944,752 A | 8/1999 | Silvestrini | |
| 5,964,748 A | 10/1999 | Peyman | |
| 6,007,578 A | 12/1999 | Schachar | 623/4 |
| 6,280,468 B1 | 8/2001 | Schachar | 623/4.1 |
| 6,299,640 B1 | 10/2001 | Schachar | 623/4.1 |

FOREIGN PATENT DOCUMENTS

| | | |
|---|---|---|
| WO | WO 96/40005 | 12/1996 |
| WO | WO 98/42409 | 10/1998 |
| WO | WO 99/17684 | 4/1999 |
| WO | WO 99/17691 | 4/1999 |
| WO | WO 00/25703 | 5/2000 |
| WO | WO 00/40174 | 7/2000 |
| WO | WO 01/17460 | 8/2000 |
| WO | WO 00/59406 | 10/2000 |

OTHER PUBLICATIONS

Schachar, et al., "Mathematic Proof of Schachar's Hypothesis of Accomodation," Ann Ophthalmol, 25: 5–9 (1993).

Schachar, et al., Experimental Support for Schachar's Hypothesis of Accommodation, Ann Ophthalmol 25: 404–409 (1993).

Schachar, et al., "A Physical Model Demonstrating Schachar's Hypothesis of Accomodation," Ann Ophthalmol 26:4–9 (1994).

Schachar, "Zonular Function: A New Hypothesis with Clinical Implications," Ann Ophthalmol 26: 36–38 (1994).

Schachar, et al., "The Effect of Gravity on the Amplitude of Accommodation," Ann Ophthalmol 26: 65–70 (1994).

Schachar, et al., "The Mechanism of Accommodation and Presbyopia in the Primate," Ann Ophthalmol 27:58–67 (1995).

Schachar, et al., "The Mechanism of Ciliary Muscle Function," Ann Ophthalmol 27:126–132 (1995).

Schachar, "Histology of the Ciliary Muscle–Zonular Connections," Ann Ophthalmol 28:70–79 (1996).

Schachar, et al., "Equatorial Diameter During Accommodation," American Physiological Society R670–R676 (1996).

Yee, et al., "Scleral Expansion: New Surgical Technique to Correct Presbyopia," Investigative Ophthalmology & Visual Science, vol. 30(4):, 5 (1997).

Glasser, et al., "Presbyopia and the Optical Changes in the Human Crystalline Lens with Age," Vision Res., 38:209–229 (1998).

Schachar, "Pathophysiology of Accommodation and Presbyopia," J. Florida M.A. 81:268–271 (1994).

Schachar, et al., "A Revolutionary Variable Focus Lens," Annals of Ophthalmology, 2811–18 (1996).

Adler–Grinberg, "Questioning Our Classical Understanding of Accommodation and Presbyopia," Am. J. Optometry & Physiological Optics, 63(7) 571–580 (1986).

Omi, et al., "Modified Schochet Implant for Refractory Glaucoma," Ophthalmology 98:211–214 (1991).

Arons, "LASIK and PRK clinical results are hot topics at the RSIG and ISRS meetings," Ocular Surgery News, http://www.slackline.com/eye/osn/19901a/lasik/asp, Jan. 1, 1999.

Atchinson, "Accommodation and Presbyopia," Ophthal Physiol. Opt. 15(4):255–272 (1995).

Bernatchez, et al., "Biocompatibility of a new semisolid bioerodable poly(orth ester) intended to the ocular delivery of 5–fluorouracil," J. Biomedical Materials Research, 28:1037–1046 (1994).

Billson, et al., "Resiting Molteno Implant Tubes," Ophthalmic Surgery and Lasers, 27:801–803 (1996).

Brockhurst, "DystrophicCalcification of Silicone Scleral Buckling Implant Materials," Am. J. Ophthalmol, 115:524–529 (1993).

Brouillette, et al., "Long–term results of modified trabeculectomy with Supramid implant for neovascular glaucoma," Can. J. Ophthalmol, 22(5):254–256 (1987).

Cameron, et al., "Clinico–histophathologic Correlation of a Successful Glaucoma Pump–shunt Implant," Ophthalmology, 95:1189–1194 (1988).

Campbell, et al., "Fluctuations of Accommodation Under Steady Viewing Conditions," J. Physiol., 145:579–594 (1959).

Coleman, et al., "Initial Clinical Experience with the Ahmed Claucoma Implant," Am. J. Ophth. 120:23–31 (1995).

Coleman, et al., "Clinical Experience with the Ahmed Glaucoma Valve Implant in Eyes with prior or Current Penetrating Keratoplasties," Am. J. Ophth., 123:54–61 (1997).

Colosi, et al., "Intrusion of Scleral Implant Associated with Conjunctival Epithelial Ingrowth," Am. J. Ophthalmol, 83:504–507 (1997).

Coltair, et al., "Scleral Pocket Incision Applied to Insertion of the Nut and Bolt Keratoprosthesis," J. Cataract Refract. Surg., 16:649–651 (1990).

Crucea, et al., "Artificial Draininge Devices in Glaucoma" Optalmologia, 47(2):5–10, Abstract only.

Daniele, et al., "Gelatin as an Absorbable Implant in Scleral Buckling Procedured," Arch Ophthal, 80:115–119 (1968).

Elander, "Scleral Expansion Sugery does not restore accommodatino in human presbyopia," J. Refract. Surg., 15(5):604 (1999).

Ellis, "Surgical Conquest of Presbyopia; Are There Implications for Cataract and Glaucoma," Refractive Surgery, 38–44 (1999).

El–Sayyad, "The Use of Releasable Sutures in Molteno Glaucoma Implants ot Reduce Postoperative Hypotony," Ophthalmic Surgery, 22:82–84 (1991).

Girard, et al., "Scleral fixation of a subluxated posterior chamber intraocular lens," J. Cataract Refract. Surg., 14:326–327 (1988).

Hashizoe, et al., "Implantable biodegradable polymeric device in the treatment of experimental proliferative vite-oretinopathy," Curr. Eye Res., 14(6):473–477 (1995).

Hashizoe, et al., "Scleral plug of biodegradable polymers for controlled drug release in the vitreous," Arch. Ophthalmol., 112(10):1380–1384 (1994).

Hashizoe, et al., "Biodetgradable polymeric devices for sustained intravitreal release of glanciclovir in rabbits," Current Eye Research, 112(10): 633–339 (1997).

Hasty, et al., "Primate Trabeculectomies with 5–fluorouracil Collagen Implants," Am. J. Ophthalmol, 109:721–725 (1990).

Hilton, et al., "The Removal of Scleral Buckles," Arch Ophthalmol, 96:2061–2063 (1978).

Ho, et al., "The MAI hydrophilic implant for scleral buckling: a view," Ophthalmic Surg., (6):611–5 (1984).

Jacklin, et al., "Gelatin as an Absorbable Implant in Scleral Buckling Procedure," Arch. Ophthalmol, 79:286–289 (1968).

Jacob, et al., "Synthetic scleral reinforcement materials. II Collagen types in the fibrous capsure," J. Biomedical Materials Research, 32:181–186 (1966).

Krupin, et al., "Filtering Valve Implant Surgery for Eyes with Neovascular Glaucoma," Am. J. Ophthalmol, 89:338–343 (1980).

Krupin, et al., "Long–Term Results of Valve Implants in Filtering Surgery Eyes with Neovascular Glaucoma," Am. J. Ophthalmol, 95:775–782 (1983).

Krupin, et al., "A Long Krupin–Denver Valve Implant Attached to a 180 Scleral Explant for Glaucoma Surgery," Ophthalmol, 95:1174–1180 (1988).

Kimura, et al., "A new Vitreal Drug Delivery System Using an Implantable Biodegradable Polymeric Device," Investigative Ophthalmol and Visual Science, 35:2815–2819 (1994).

King, et al., "Gelatin Implants in Scleral Buckling Procedures," Arch. Ophthalmol., 93:807–811 (1975).

Lambert, et al., "Wedge Implant Used as an Explant," Am. J. Ophthalmol., 101:488–489 (1986).

Lambert, et al., "A New Alloplastic Material for Opthalmic Surgery," Ophthalmic Surgery, 9:35–42 (1978).

Law, et al., "Retinal Complications after Aqueous Shunt Surgical Procedures for Glaucoma," Arch Ophthalmol, 114:1473–1480 (1996).

Levit, et al., "Use of Ophthalmic Gelfilm in retinal Surgery," Ann. Ophthalmol, 1613–16161 (Dec. 1975).

Lipner, "A Closer Look at Scleral Surgery," Eyeworld (Sep. 13, 1999) http://www.eyeworld.org/sep99/999p34.asp.

Lincoff, et al., "The Changing Character of the Infected Scleral Implant," Arch. Ophthalmol, 84:421 et seq (1970).

Liu, et al., "Scleral Buckling with a Soft Xerogel Implant: II Experiments in Vivo," Ophthalmic Surgery, 10:52–56 (1979).

Lloyd, et al., "Initial Clinical Experience with Baeveldt Implant in Complicated Glaucomas," Ophthalmology, 101:650–640 (1994).

Luttrull, et al., "Pars Plana Implant and Vitrectomy for Treatment of Neovascular Glaucoma," Retina, 15:379–387 (1995).

Luttrull, et al., "Initial Experience with Pneumatically Stented baerveldt implant modifiedfor Pars Plana Insertion in Complicated Glaucoma," Ophthalmology, 107:143–149 (2000).

Marin, et al., "Long–term Complications of the MAI Hydrogel Intrascleral Buckling Implant," Arch. Ophthalmol, 110:86–88 (1992).

Matthews, et al., Scleral Expansion Surgery Does Not Restore Accommodation in Human Prosbyopia, Ophthalmology, 106:873–877 (1999).

Melamed, et al., "Molteno Implant Surgery in Refractory Glaucoma," Survey of Ophthalmology, 34:441–448 (1990).

Minckler, et al., Clinical Experience with the Single–plate Molteno Implant in Complicated Glaucomas, Ophthalmology 95:1181–1188 (1988).

Miyamoto, et al., "Biodegradable Scleral Implant for Controlled Release of Flocanazole," Current Eye Research, 16:930–935 (1997).

Ocular Surgery News, "Presbyopia Reversible in Pilot Studies," Jul. 1, 1999; http://www.slackinc.com/eve/osn/199907a/presby.asp.

Peiffer, et al., "Long–term Comparative Study of the Schochet and Joseph Glaucoma Tube Shunts in Monkeys," Ophthalmic Surgery, 21:55–59 (1990).

Pruett, "The Fishmouth Phenomenon," Ach. Ophthalmol, 95:1777–181 (1977).

Rabowsky, et al., "The Use of Biorodeable Polymers and Daunarubicin in Glaucoma Filtration Surgery," Ophthalmology, 103:800–807 (1996).

Ray, et al., "Gelatin Implants in Scleral Buckling Procedures," Arch Ophthalmol, 93:799–802 (1975).

Refojo, "Polymers in Ophthalmic Surgery," J. Biomed. Mater. Res., 5:113–119 (1971).

Refojo, et al., "Experimental Scleral Buckling with a Soft Xerogel Implant," Ophthalmic Surgery, 9:43–50 (1978).

Riggs, et al., "Intraocular Silicone Prostheses in a Dog and a Horse with Corneal Lacerations," J. Am. Vet. Med. Assoc., 196:617–619 (1990).

Rohr, et al., "Surgical Correction of Presbyopia," J. Osteopathic College of Ophthalmology and Otohinolaryngology, 12:34–36 (2000).

Rubsamen, et al., "Prevention of Experimental Poliferative Vitreoretinopathy with a Biodegradable Intravitreal Implant for the Sustained Release of Fluoroacil," Arch. Ophthalmol. 112:407–413 (1994).

Sakamoto, et al., "Silicone Sponge Implant in Combination with Episcleral Implant for Retinal Surgery," Ophthalmic Surgery, 11:712–718 (1980).

Sarkies, et al., "Silicone Tube and Gutter in Advanced Glaucoma," Trans. Ophthalmol, Soc. U.K., 144:133–136 (1985).

Schepens, et al., "Scleral Implants: An Historic Perspective, "Survey of Ophthalmology, 35:447–453 (1991).

Sherwood, et al., "Surgery for Refractory Glaucoma," Arch. Ophthalmol, 105:562–569 (1987).

Sidoti, et al., "Epithelial Ingrowth and Glaucoma Drainage Implants," Ophthalmol, 101:872–875 (1994).

Sidoti, et al., "Aqueous Tube Shunt to a Pre–existing Episcleral Encircling Element in the Treatment of Complicated Glaucomas," Ophthalmol, 101:1036–1043 (1994).

Smith, et al., "One–year results of the intrascleral glaucoma implant," J Cataract Refract. Surg., 21:453–456 (1995).

Smith, et al., "Comparison of the Double–Plate Molteno Drainage Implant with the Schochet Procedure," Arch. Ophthalmol, 110:1246–1250 (1992).

Speigel, et al., "Anterior Chamber Tube Shunt to an Encircling Band (Schochet procedure) in the Treatment of Refractory Glaucoma," Ophthalmic Surgery, 12:804–807 (1992).

Strubble, et al., "In vitro low characteristics of the Amhed and self–constructed anterior chamber shunts," Am. J. Vet. Res., 58:1332–1337 (1997).

Sveinsson, et al., "Trabeulectomy and gelatin implants," Acta Ophthalmologica, 70:645–650 (1992).

Susanna, "Modifications of the Molteno Implants and implant Procedure," Ophthalmic Surgery, 22:611–613 (1991).

Szymanski, "Scleral free auto–implant plug with mitomycin as limitation of trepanosclerectomy flow in glucoma filtering surgery," International Ophthalmology, 20:89–94 (1997).

Tanji, et al., "Fascia Lata Patch Graft in Glaucoma Tube Surgery," Ophthalmology, 103:1309–1312 (1996).

Tawakol, et al., "Gore–Tex Soft Tissue Bands as Scleral Explants in Rabbits: A Preliminary Histologic Study," Ophthalmic Surgery, 20:199–201 (1989).

Watzke, "Scleral Patch Graft for Exposed Episcleral Implants," Arch Ophthalmol, 102:114–115 (1984).

Wilson, et al., "New hope for presbyopia: PMMA scleral bands show primise," Eyeworld, (1999); http://www.eyeworld.org/apr98/963.html.

Wilson, et al., "Aqueous Shunts—Molteni versus Schocket," Ophthalmology, 99:672–678 (1992).

Wilson–Holt, et al., "Hypertrophy flowing insertion of inferiorly sited double–plate Molteno tubes," Eye, (Pt. 5): 515–20 (1992).

Yoshizumi, "Exposure of Intrascleral Implants," Ophthalmology, 87:1150–1154 (1980).

Yoshizumi, "Erosion of Implants in Retinal Detachment Surgery," Annals of Ophthalmology, 87:430–434 (1983).

Banuelos et al., "Expandable Silicone Implants for Scleral Buckling," Arch Ophthalmol, 89:500–502 (1973).

* cited by examiner

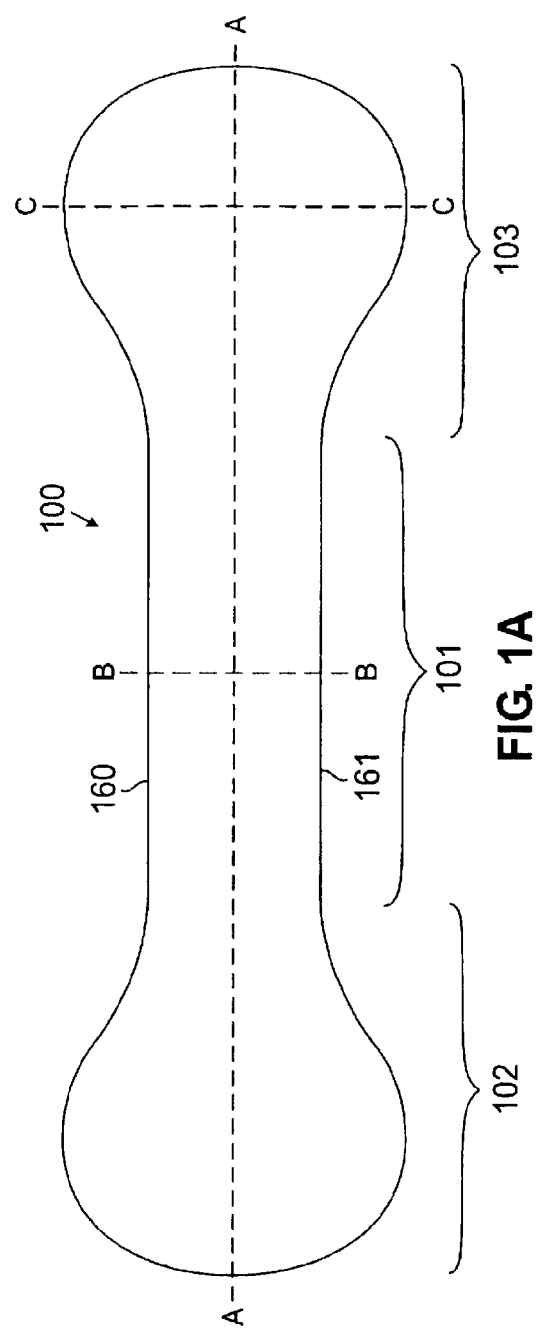
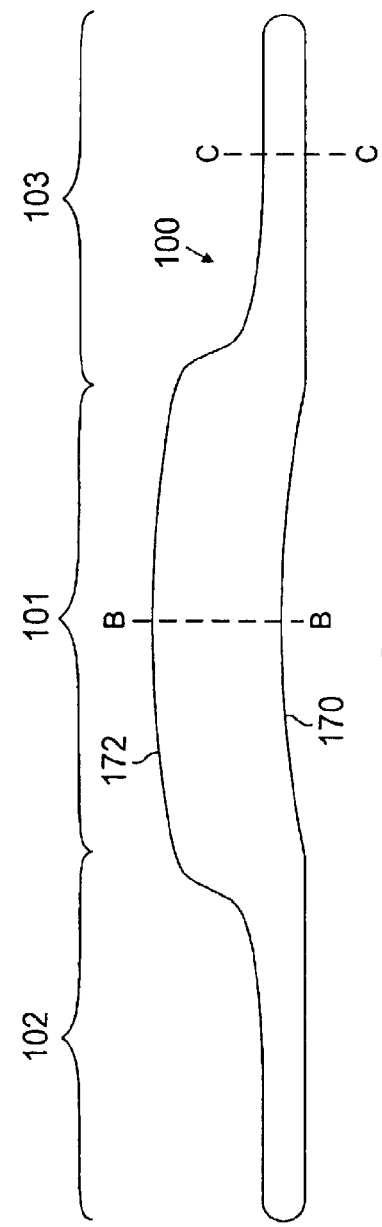
FIG. 1A
FIG. 1B

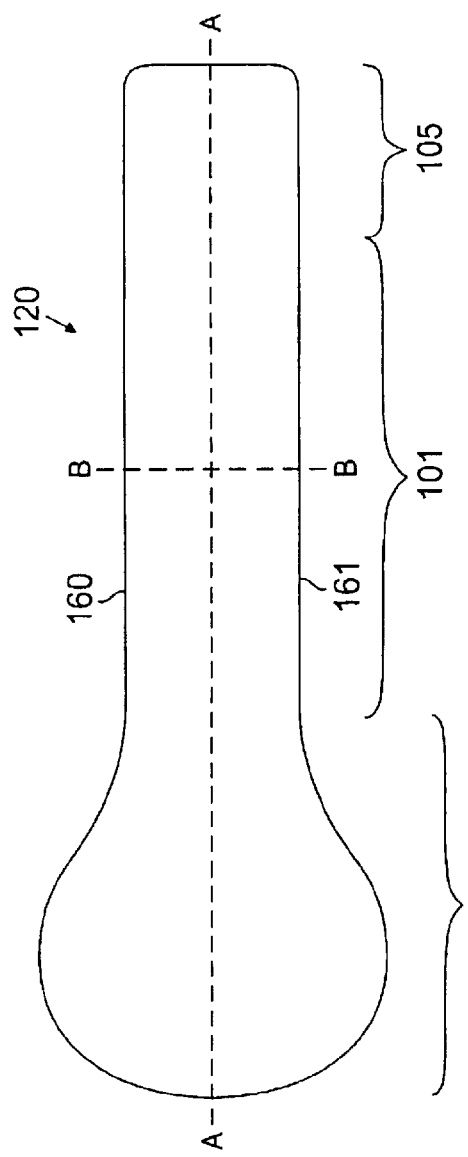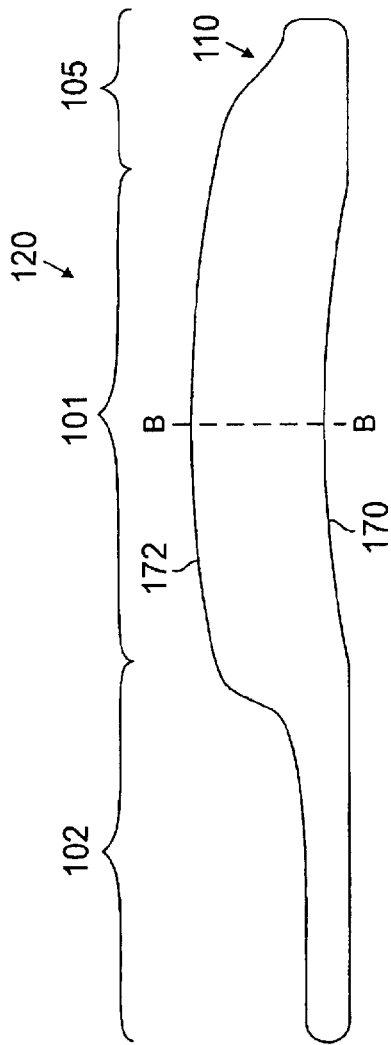

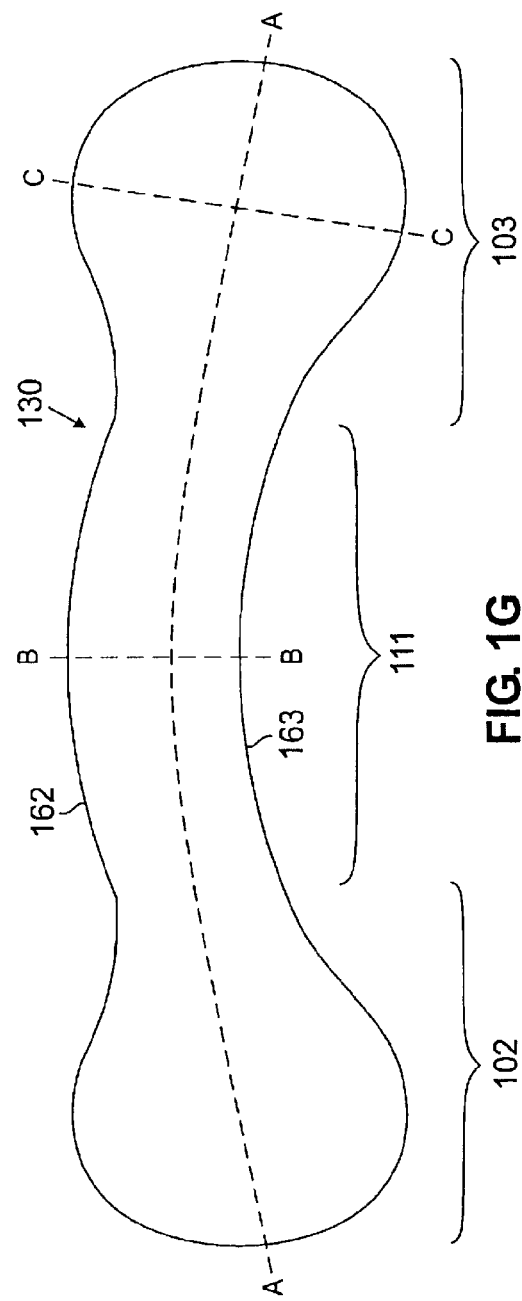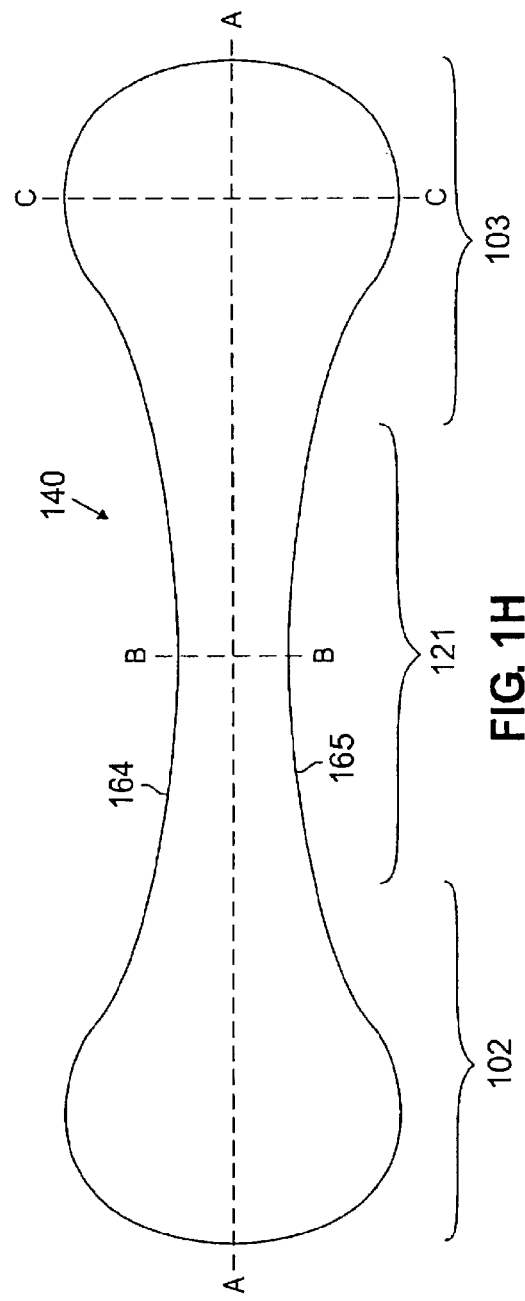

SCLERAL EXPANSION DEVICE HAVING DUCK BILL

CROSS REFERENCE TO RELATED APPLICATIONS

This application claims priority under 35 U.S.C. § 119(e)(1) to U.S. Provisional Patent Application No. 60/206,134 filed May 22, 2000, and is a continuation-in-part of: (1) U.S. patent application Ser. No. 09/061,168, entitled "SCLERAL PROSTHESIS FOR TREATMENT OF PRESBYOPIA AND OTHER EYE DISORDERS" and filed on Apr. 16, 1998 now U.S. Pat. No. 6,280,468, which application is a continuation-in-part of U.S. patent application Ser. No. 08/946,975 entitled "SCLERAL PROSTHESIS FOR TREATMENT OF PRESBYOPIA AND OTHER EYE DISORDERS" and filed Oct. 8, 1997, now U.S. Pat. No. 6,007,578 issued Dec. 28, 1999; (2) U.S. patent application Ser. No. 09/472,535 entitled "SCLERAL PROSTHESIS FOR TREATMENT OF PRESBYOPIA AND OTHER EYE DISORDERS" and filed Dec. 27, 1999 now U.S. Pat. No. 6,299,640, which application is a continuation of U.S. patent application Ser. No. 08/946,975; (3) U.S. patent application Ser. No. 09/589,626 entitled "IMPROVED SCLERAL PROSTHESIS FOR TREATMENT OF PRESBYOPIA AND OTHER EYE DISORDERS" and filed Jun. 7, 2000, which application is a continuation-in-part of U.S. patent applications Ser. Nos. 08/946,975, 09/061,168 and 09/472,535, All of the above-identified documents, and the inventions disclosed therein, are incorporated herein by reference for all purposes as if fully set forth herein.

TECHNICAL FIELD OF THE INVENTION

This invention relates to methods of treating presbyopia, hyperopia, primary open angle glaucoma and ocular hypertension and more particularly to methods of treating these diseases by increasing the effective working distance of the ciliary muscle. The invention also relates to increasing the amplitude of accommodation of the eye by increasing the effective working range of the ciliary muscle.

BACKGROUND OF THE INVENTION

In order for the human eye to have clear vision of objects at different distances, the effective focal length of the eye must be adjusted to focus the image of the object as sharply as possible on the retina. Changing the effective focal length is known as accommodation, and is accomplished in the eye by varying the shape of the crystalline lens. Generally the curvature of the lens in an unaccommodated emmetropic eye allows distant objects to be sharply imaged on the retina, while near objects are not focused sharply on the retina in the unaccommodated eye because the image lie behind the retinal surface. In order to perceive a near object clearly, the curvature of the crystalline lens is increased, thereby increasing the refractive power of the lens and causing the image of the near object to fall on the retina.

The change in shape of the crystalline lens is accomplished by the action of certain muscles and structures within the eyeball or globe of the eye. As described in greater detail in, for example, U.S. Pat. No. 6,146,366, the lens has the shape of a classical biconvex optical lens—that is, generally circular with two convex refracting surfaces-and is located in the forward part of the eye immediately behind the pupil and generally on the optical axis of the eye (i.e., a straight line drawn from the center of the cornea to the macula in the retina at the posterior portion of the globe). In the unaccommodated human eye the curvature of the posterior surface of the lens (the surface adjacent to the vitreous body) is somewhat greater than that of the anterior surface.

The lens is closely surrounded by a membranous capsule that serves as an intermediate structure in the support and actuation of the lens. The lens and the capsule are suspended on the optical axis behind the pupil by a circular assembly of many radially directed elastic fibers, the zonules, which are attached at inner ends to the lens capsule and at outer ends to the ciliary muscle, a muscular ring of tissue located just within the outer supporting structure of the eye, the sclera. The ciliary muscle is relaxed in the unaccommodated eye and therefore assumes a maximum diameter. According to the classical theory of accommodation, originating with Helmholtz, the relatively large diameter of the ciliary muscle in this condition causes a tension on the zonules, which in turn pull radially outward on the lens capsule and cause the equatorial diameter of the lens to increase slightly while decreasing the anterior-posterior dimension (thickness) of the lens at the optical axis. Thus, the tension on the lens capsule causes the lens to assume a flattened state wherein the curvature of the anterior surface, and to some extent the posterior surface, is less than the curvature which would exist in the absence of the tension. In this state the refractive power of the lens is relatively low and the eye is focused for clear vision for distant objects.

To focus the eye on a near object, the ciliary muscles contract. According to the classical theory, this contraction causes the ciliary muscle to move forward and inward, thereby relaxing the outward pull of the zonules on the equator of the lens capsule. Such reduced zonular tension allows the elastic capsule of the lens to contract, causing an increase in the antero-posterior diameter (thickness) of the lens (i.e., the lens becomes more spherical) and resulting in an increase in the optical power of the lens. Because of topographical differences in the thickness of the lens capsule, the central anterior radius of curvature decreases more than the central posterior radius of curvature. This constitutes the accommodated condition of the eye, wherein the image of near objects falls sharply on the retina.

Presbyopia is the universal decrease in the amplitude of accommodation that is typically observed in individuals over 40 years of age. In the person having normal vision (i.e., having emmetropic eyes) the ability to focus on near objects is gradually lost, and the individual comes to need glasses for tasks requiring near vision, such as reading.

According to the conventional view the amplitude of accommodation of the aging eye is decreased because of the loss of elasticity of the lens capsule and/or sclerosis of the lens with age. Consequently, even though the radial tension on the zonules is relaxed by contraction of the ciliary muscles, the lens does not assume a greater curvature. According to the conventional view, treatment to restore the accommodative power to the presbyopic eye is not possible. The loss of elasticity of the lens and capsule is seen as irreversible, and the only solution to the problems presented by presbyopia is to use corrective lenses for close work, or bifocal lenses, if corrective lenses are also required for distant vision.

In contrast to the conventional (Helmholtz) theory, the Schachar theory of accommodation—on which the related patent applications identified above are based—postulates that outward equatorial displacement of the crystalline lens produces a central steepening (and peripheral flattening) of the lens surface. The equatorial displacement results from increased tension on the equatorial zonules which is produced, in turn, by contraction of the anterior radial muscle fibers of the ciliary muscle. Since active force is involved in accommodation, the amount of force which may be applied to the lens equator is dependent on how much the ciliary muscle is stretched. Since the crystalline lens is of ectodermal origin and continues to grow throughout the life of an individual while the dimensions of the scleral shell do not change significantly after 13 years of age (with certain exceptions), the distance between the ciliary muscle and the equator of the lens decreases throughout the life of an individual. Therefore, the effective force which the ciliary muscle may apply to the lens equator is reduced with age, such that the decrease in the amplitude of accommodation resulting in presbyopia is a consequence of normal lens growth.

Such continued lens growth decreases the working distance of the zonules and ciliary muscle, decreasing the range of accommodation which may be achieved by contracting the ciliary muscle to a point where focusing near objects on the retina is no longer possible. Under this view, presbyopia may be suitably treated by increasing the effective working distance of the ciliary muscle, such as by increasing the distance between the ciliary muscle and the lens equator, preferably by increasing the diameter of the sclera (i.e., scleral expansion) in the region of the ciliary body.

Prostheses have been disclosed in the related applications identified above for treating presbyopia by implantation within a number of elongated pockets formed in the sclera of the eye transverse to a meridian of the eye, expanding the sclera and restoring the effective working distance of the ciliary muscle. However, as disclosed in Ser. No. 09/589,626 ("the '626 application"), such prostheses may exhibit a tendency to slide back and forth within the scleral pocket or to turn or topple over within the scleral pocket, reducing the effectiveness of the prostheses in treating presbyopia in either case. In particular, prosthesis embodiments which have a circumferential shape including a curved bottom surface may have limited surface contact between the bottom surface and the inner wall of the surgically formed scleral pocket, generally in the area of the first and second ends of the prosthesis, and therefore suffer stability problems due at least in part, to the disproportionate surface contact of the top surface of the prosthesis relative to the bottom surface.

There is, therefore, a need as disclosed in the '626 application to improve the stability of a prosthesis inserted within a scleral pocket for treatment of presbyopia and other eye disorders.

SUMMARY OF THE INVENTION

A prosthesis for scleral expansion includes a central body portion and at least one end portion having a width greater than the width of the central body portion. The end portion therefore inhibits rotation of the prosthesis about a long axis when the prosthesis is implanted within a scleral pocket or tunnel. The other end of the central body portion may have a blunted end portion including grooves for receiving a edge or lip of an incision forming the scleral tunnel to inhibit the prosthesis from sliding within the scleral tunnel. Curvature of the bottom surface of the central body portion may be greater than the curvature of the innermost surface of the scleral tunnel so that contact between the scleral and the bottom surface of the prosthesis is primarily with the end portions.

The foregoing has outlined rather broadly the features and technical advantages of the present invention so that those skilled in the art may better understand the detailed description of the invention that follows. Additional features and advantages of the invention will be described hereinafter that form the subject of the claims of the invention. Those skilled in the art should appreciate that they may readily use the conception and the specific embodiment disclosed as a basis for modifying or designing other structures for carrying out the same purposes of the present invention. Those skilled in the art should also realize that such equivalent constructions do not depart from the spirit and scope of the invention in its broadest form.

BRIEF DESCRIPTION OF THE DRAWINGS

An advantageous embodiment of the present invention may be understood with reference to the following descriptions taken in conjunction with the accompanying drawings, wherein like numbers designate like objects, in which:

FIGS. 1A and 1B are a top plan view and a side elevation view, respectively, of a prosthesis for increasing the effective working distance of the ciliary muscle by implantation into surgically formed scleral tunnels according to one embodiment of the present invention;

FIGS. 1E and 1F are a top plan view and a side elevation view, respectively, of a prosthesis for increasing the effective working distance of the ciliary muscle by implantation into surgically formed scleral pockets or tunnels according to another embodiment of the present invention;

FIG. 1G is a top plan view of a prosthesis for increasing the effective working distance of the ciliary muscle by implantation into surgically formed scleral tunnels according to another embodiment of the present invention;

FIG. 1H is a top plan view of a prosthesis for increasing the effective working distance of the ciliary muscle by implantation into surgically formed scleral tunnels according to another embodiment of the present invention;

DETAILED DESCRIPTION OF THE INVENTION

Figure 1C:
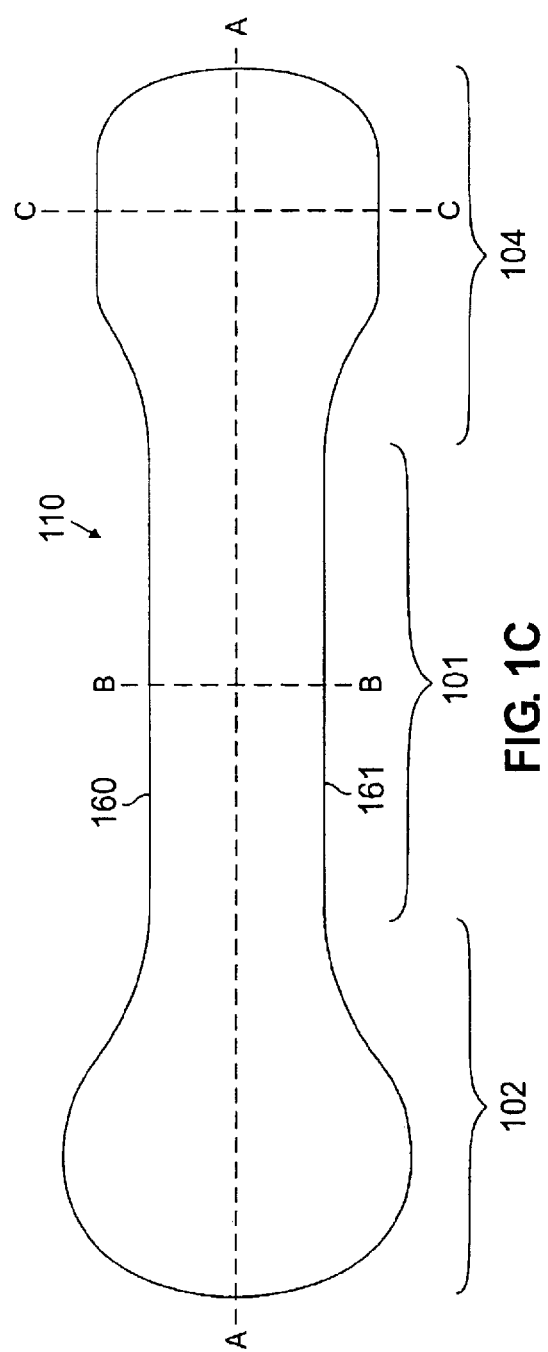
FIGS. 1C and 1D are a top plan view and a side elevation view, respectively, of a prosthesis for increasing the effective working distance of the ciliary muscle by implantation into surgically formed scleral tunnels according to another embodiment of the present invention.

According to present invention, presbyopia and certain other eye disorders (e.g., hyperopia, primary open angle glaucoma, ocular hypertension, etc.) may suitably be treated by increasing the effective working distance of the ciliary muscle. Such increase may be achieved by increasing the distance between the ciliary muscle and the lens equator, preferably by increasing the diameter of the sclera (i.e., scleral expansion) in the region of the ciliary body. According to one embodiment of the present invention, the effective working distance of the ciliary muscle may suitably be increased by implanting, within pockets surgically formed in the sclera of the eye, a plurality of prostheses designed to place an outward traction on the sclera in the region of the ciliary body.

FIGS. 1A and 1B are a top plan view and a side elevation view, respectively, of a prosthesis for increasing the effective working distance of the ciliary muscle by implantation into surgically formed scleral tunnels according to one embodiment of the present invention. Prosthesis 100 includes a central body portion 101 connecting end portions 102 and 103. As with the prostheses described in the related applications described above, prosthesis 100 is intended to be inserted within a surgically formed pocket or tunnel within the sclera, elevating a portion of the sclera to increase the effective working distance of the ciliary muscle.

The planform of exemplary prosthesis 100 of FIGS. 1A–1B includes "duck bill" end portions 102 and 103 which are wider and flatter (and, in the exemplary embodiment, thinner) than the intermediate central body portion 101. These "duck bill" end portions promote stability when the prosthesis 100 is within the scleral tunnel, inhibiting the prosthesis 100 from turning or toppling over (i.e., rotating about a long axis of the prosthesis 100) within the scleral tunnel.

When prosthesis 100 is inserted within a scleral tunnel, essentially all of central body portion 101 is preferably contained within the tunnel, while essentially all of end portions 102 and 103 are preferably outside the scleral tunnel (i.e., the scleral tunnel has a length approximately equal to the length of central body portion 101 of prosthesis 100). In such instances, central body portion 101 is within the sclera or under the scleral layer, while end portions 102 and 103 are on the sclera, a bottom surface of end portions 102 and 103 in contact with an outer surface of the sclera. Alternatively, however, one or more portions of central body portions 101 proximate to end portions 102 and/or 103 may be outside the scleral tunnel, or one or more portions of end portions 102 and/or 103 may be within the tunnel (i.e., the scleral tunnel has a length which is either greater than or less than the length of central body portion 101 of prosthesis 100).

Figure 1D:
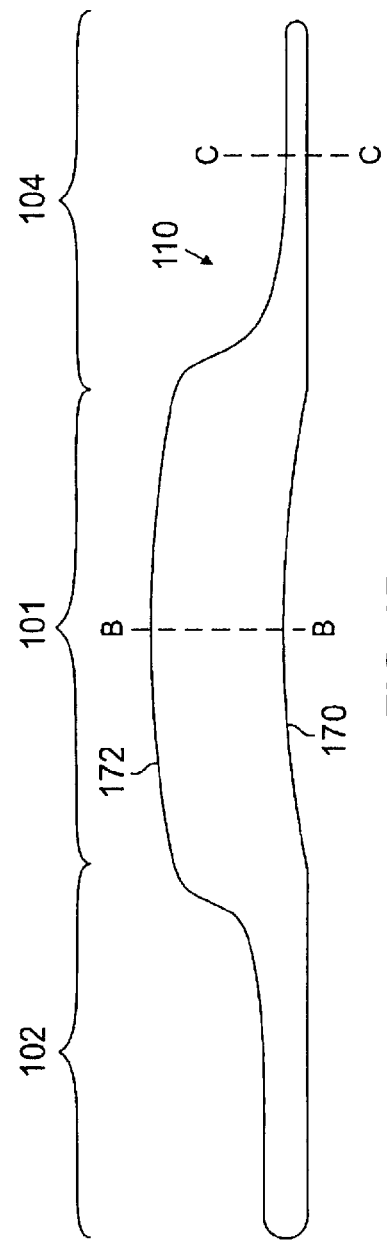

FIGS. 1C and 1D are a top plan view and a side elevation view, respectively, of a prosthesis for increasing the effective working distance of the ciliary muscle by implantation into surgically formed scleral tunnels according to another embodiment of the present invention. In the embodiment of FIGS. 1C–1D, one duck bill end portion 102 projecting from the central body portion 101 of the prosthesis 110 is wider and/or thicker than the other duck bill end portion 104. During insertion of the prosthesis 110 within a scleral tunnel, narrower and/or thinner end portion 104 is intended to be passed through both incisions within the sclera which form the ends of the scleral tunnel. The benefits of having one duck billed end portion 104 which is narrower and/or thinner than the other is addressed in further detail below.

FIGS. 1E and 1F are a top plan view and a side elevation view, respectively, of a prosthesis for increasing the effective working distance of the ciliary muscle by implantation into surgically formed scleral pockets or tunnels according to another embodiment of the present invention. Prosthesis 120 in the embodiment of FIGS. 1E–1F includes only duck billed end portion 102 projecting from the central body portion 101. The other end of the central body portion may have no end portion, or, as shown in the example of FIGS. 1E–1F, may have an end portion 105 which is not wider than central body portion 101. In the example shown, blunted end portion 105 is not as long as duck bill end portion 102. However, blunted end portion 105 is substantially thicker than duck bill end portion 102, tapering from the thickness of central body portion 101 to an end thickness to a lesser degree than does duck bill end portion 102.

Prosthesis 120 may be implanted in a scleral pocket (i.e., a passage either into and along or through or under the scleral layer which has only on opening) rather than a scleral tunnel (a passage either into, along and out of the scleral layer of through, under and back through the scleral layer, with two openings, one at either end). Preferably, however, prosthesis 120 is implanted in a scleral tunnel with substantially all of central body portion 101 within the scleral tunnel (either within or under the scleral layer) while duck bill end portion 102 and blunted end portion 105 are both substantially outside the scleral tunnel resting on the outer surface of the sclera. Advantages of having blunted end portion 105 outside the scleral tunnel are described in further detail below.

Dashed line 190 within duck bill end portion 102 illustrates that the end portions which are wider than the central body portions of a prosthesis need not increase in width uniformly in both directions (on both sides), but may instead increase in width only on one side with the other side retaining planar alignment with the side of the central body portion.

FIG. 1G is a top plan view of a prosthesis for increasing the effective working distance of the ciliary muscle by implantation into surgically formed scleral tunnels according to another embodiment of the present invention. The planform of the central body portion 111 for prosthesis 130 in FIG. 1G is circumferential—that is, shaped to follow a portion of a circle around the lens of the eye. While the sides surfaces 160 and 161 of central body portion 101 depicted in FIGS. 1A, 1C and 1E are straight along a long axis of the respective prosthesis 100, 110 or 120, the side surfaces 162 and 163 of prosthesis 130 are both curved along the long axis of prosthesis 130. Side surfaces 162 and 163 are both curved in the same direction (with side surface 162 being convex and side surface 163 being concave) and preferably having a common focal point for the radius of curvature. However, the two sides 162 and 163 may have differing degrees of curvature (i.e., each having a different focal point for the respective radius of curvature). The prosthesis 130 of FIG. 1G is intended to be implanted within a scleral tunnel with side surface 162 further from the lens than side surface 163. Use of an end portion which widens only on one side (e.g., the outer edge) may be useful in this embodiment and other embodiments where rotation of the implanted prosthesis is much more likely in one direction than in the opposite direction.

FIG. 1H is a top plan view of a prosthesis for increasing the effective working distance of the ciliary muscle by implantation into surgically formed scleral pockets or tunnels according to another embodiment of the present invention. While the sides surfaces 160 and 161 of central body portion 101 depicted in FIGS. 1A, 1C and 1E are straight along a long axis of the respective prosthesis 100, 110 or 120 and the side surfaces 162 and 163 of the central body portion 111 depicted in FIG. 1G are both curved in the same direction, side surfaces 164 and 165 of the central body portion 121 for prosthesis 140 are curved, along the long axis of prosthesis 140, in opposite directions. In the example shown, both side surfaces 164 and 165 are concave, and have identical curvatures (i.e., the same radius of curvature, although with different focal points). However, the side surfaces may alternatively both be convex and/or may have different curvatures.

In the example shown, end portions 102 and 103 are wider than the wide point(s) of central body portion 121 (i.e., the ends of the central body portion 121 for the embodiment depicted in FIG. 1H). In accordance with the present invention, however, end portions 102 and 103 need only be wider than some portion of central body portion 121 (i.e., should be wider than the narrowest portion of central body portion 121) to improve stability of the prosthesis 140 within the scleral tunnel.

It should be noted that while prostheses 130 and 140 are depicted in FIGS. 1G and 1H as having equally sized duck bill end portions 102 and 103 as described above with respect to prosthesis 100 depicted in FIG. 1A and 1B, either prosthesis 130 or 140 may instead include a duck bill end portion at one end of central body portion 111 or 121 which is smaller and/or thinner than the duck bill end portion at the opposite end, in the manner of prosthesis 110 depicted in FIGS. 1C and 1D (end portions 102 and 104). Likewise, either prosthesis 130 or 140 may alternatively include a duck bill end portion at one end of central body portion 111 or 121 and a blunted end portion at the opposite end, in the manner of prosthesis 120 depicted in FIGS. 1E and 1F (end portions 102 and 105).

Figure 1I:
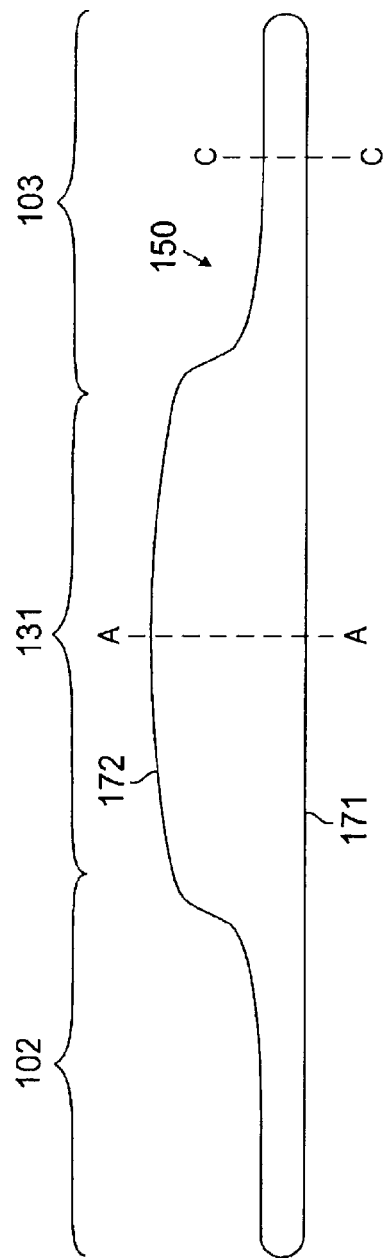
FIG. 1I is a side elevation view of a prosthesis for increasing the effective working distance of the ciliary muscle by implantation into surgically formed scleral tunnels according to another embodiment of the present invention.

FIG. 1I is a side elevation view of a prosthesis for increasing the effective working distance of the ciliary muscle by implantation into surgically formed scleral tunnels according to another embodiment of the present invention. While the bottom surface 170 of the central body portion 101 depicted in FIGS. 1B, 1D and 1F is curved (concave) along a long axis of the prosthesis 100, 110 or 120, prosthesis 150 includes a central body portion 131 having a bottom surface 171 which is straight along the long axis of prosthesis 150 (but which may be curved in other directions, as described in further detail below). Alternatively, the bottom surface of the central body portion may be convex along the long axis of the prosthesis.

Central body portions 111 and 121 depicted in FIGS. 1G and 1H may have a bottom surface which is concave along the long axis of the respective prosthesis 130 or 140, similar to central body portion 101 in FIGS. 1B, 1D and 1F, flat along the long axis in the manner depicted for central body portion 131 depicted in FIG. 1I, or convex along the long axis. Moreover, while prostheses 150 is depicted in FIG. 1I as having equally sized duck bill end portions 102 and 103 as described above with respect to prosthesis 100 depicted in FIGS. 1A and 1B, prosthesis 150 may instead include either: (1) a first duck bill end portion at one end of central body portion 131 which is smaller and/or thinner than a second duck bill end portion at the opposite end, in the manner of prosthesis 110 depicted in FIGS. 1C and 1D (end portions 102 and 104); or (2) a duck bill end portion at one end of central body portion 131 and a blunted end portion at the opposite end, in the manner of prosthesis 120 depicted in FIGS. 1E and 1F (end portions 102 and 109).

Figure 1J:
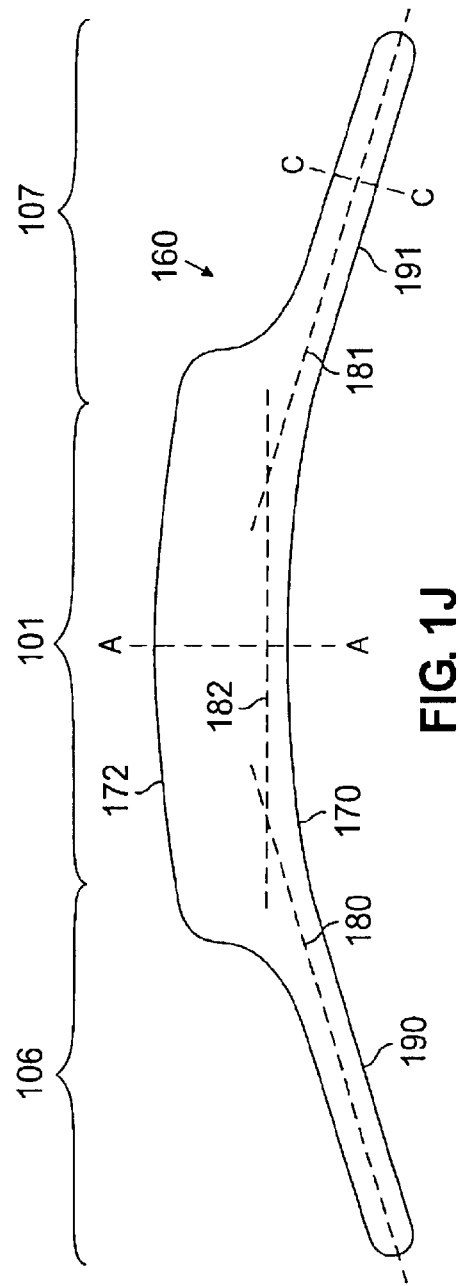
FIG. 1J is a side elevation view of a prosthesis for increasing the effective working distance of the ciliary muscle by implantation into surgically formed scleral tunnels according to another embodiment of the present invention.

FIG. 1J is a side elevation view of a prosthesis for increasing the effective working distance of the ciliary muscle by implantation into surgically formed scleral tunnels according to another embodiment of the present invention. While the end portions 102-105 are depicted in FIGS. 1B, 1D, 1F and 1I as being substantially aligned with the respective central body portion 101 or 131, end portions 106 and 107 in prosthesis 160 are angled with respect to central body portion 101. That is, the planes 180 and 181 with which end portions 106 and 107 are aligned (taken with respect to the bottom surfaces 190 and 191 of end portions 106 and 107) are angled with respect to, and intersect, the plane 182 with which central body portion 101 or 131 is aligned (again, taken with respect to the bottom surface 170 or 171 of central body portion 101 or 131). By contrast, the planes with which end portions 102–105 are aligned are at least parallel with the planes to which central body portions 101 and 131 are aligned; end portions 102–105 and central body portions 101 and 131 may, in fact, be aligned with the same plane.

Such angling of end portions 106 and 107 with respect to the central body portion 101 is preferably sufficient to allow the bottom surfaces 190 and 191 to be substantially tangential to the surface of the sclera on which such end portions 106 and 107 rest when prosthesis 160 in implanted within a scleral tunnel. End portions 102, 103 and/or 104 may also be angled with respect to the corresponding central body portions 101, 111, 121 or 131 in the prostheses 120, 130, 140 and 150 depicted in FIGS. 1C and 1F through 1I. Moreover, only one end portion (e.g., end portion 102) may be angled with respect to a central body portion, while the opposite end portion (e.g., duck bill end portion 104 or blunted end portion 105) may be substantially aligned with the corresponding central body portion.

Those skilled in the art will understand that any of the various alternative embodiments described or suggested above which includes either no end portion or a blunted end portion at one end of the respective prosthesis may be implanted within a scleral pocket rather than a scleral tunnel.

Figure 2A:
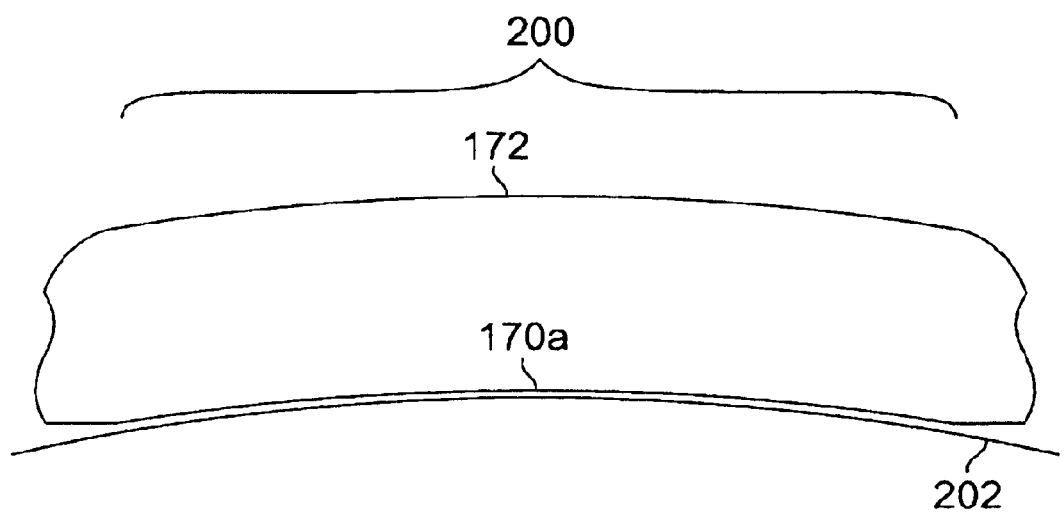
FIGS. 2A and 2B are longitudinal cross-sectional views of the central body portion of a prosthesis for increasing the effective working distance of the ciliary muscle by implantation into surgically formed scleral pockets or tunnels according to various alternative embodiments of the present invention.
Figure 2B:
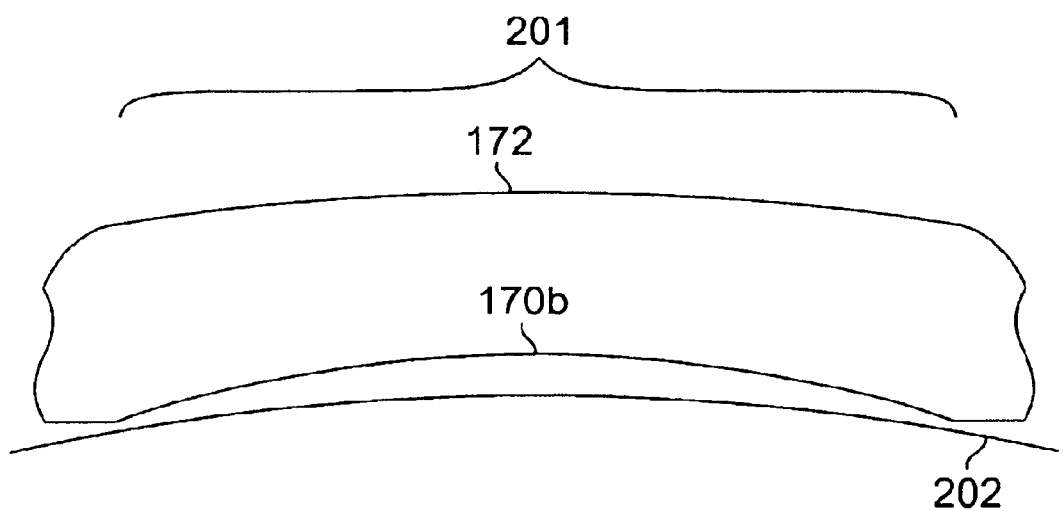

FIGS. 2A and 2B are longitudinal cross-sectional views of the central body portion of a prosthesis for increasing the effective working distance of the ciliary muscle by implantation into surgically formed scleral pockets or tunnels according to various alternative embodiments of the present invention. FIGS. 2A and 2B depict a cross-section taken along section lines A—A, along a long axis of the prosthesis, with the end portions broken away. The central body portion cross-sections 200 and 201 depicted in FIGS. 2A and 2B may correspond to any of central body portions 101, 111 or 121 depicted in FIGS. 1A–1H and 1J.

As shown in both central body portion cross-sections 200 and 201, the top surface 172 of the central body portion has a convex curvature along the long axis of the respective prosthesis (e.g., prosthesis 100, 110, 120, 130, 140 or 160). Alternatively, the top surface of the central body portion may be straight or have a concave curvature.

As illustrated in FIGS. 1B, 1D, 1F and 1J, bottom surface 170 has a concave curvature along a long axis of the respective prosthesis. The bottom surface 170a may have a curvature which is approximately equal to a curvature of the innermost surface 202 of the scleral tunnel into which the prosthesis is to be implanted (i.e., the curvature of the remaining scleral layer underlying the scleral tunnel for an intra-scleral tunnel or, where the scleral tunnel is formed between the sclera and the underlying tissue, of the tissue underlying the scleral layer).

As illustrated in FIG. 2B and described in the '626 application, however, the bottom surface 170b may have a curvature which is greater than the curvature of the innermost surface 202 of the scleral tunnel (i.e., a smaller radius of curvature), such that the prosthesis rests primary on the end portions and/or end regions of the central body portion when implanted, with the bottom surface 170b in a middle area of the central body portion spaced apart from the underlying innermost surface 202 of the scleral tunnel.

FIGS. 3A through 3E are transverse cross-sectional views of the central body portion of a prosthesis for increasing the effective working distance of the ciliary muscle by implantation into surgically formed scleral pockets or tunnels according to various alternative embodiments of the present invention. FIGS. 3A through 3E depict a cross-section taken along section lines B—B, transverse to a long axis of the prosthesis. The central body portion cross-sections depicted in FIGS. 3A through 3E may correspond to any of central body portions 101, 111, 121 or 131 depicted in FIGS. 1A–1J.

Figure 3A:
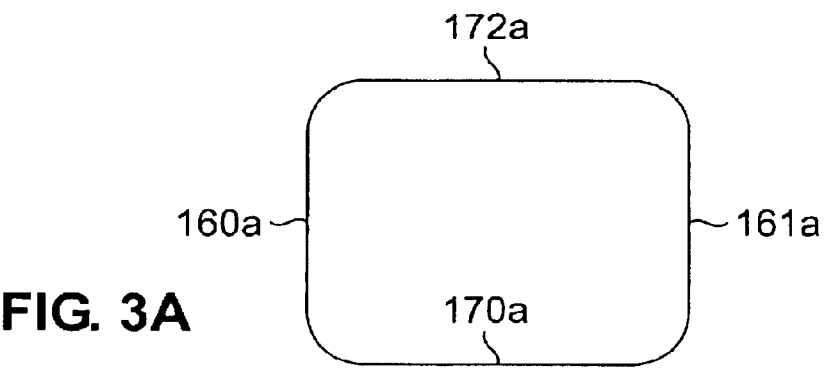
FIGS. 3A through 3E are transverse cross-sectional views of the central body portion of a prosthesis for increasing the effective working distance of the ciliary muscle by implantation into surgically formed scleral pockets or tunnels according to various alternative embodiments of the present invention.
Figure 3B:
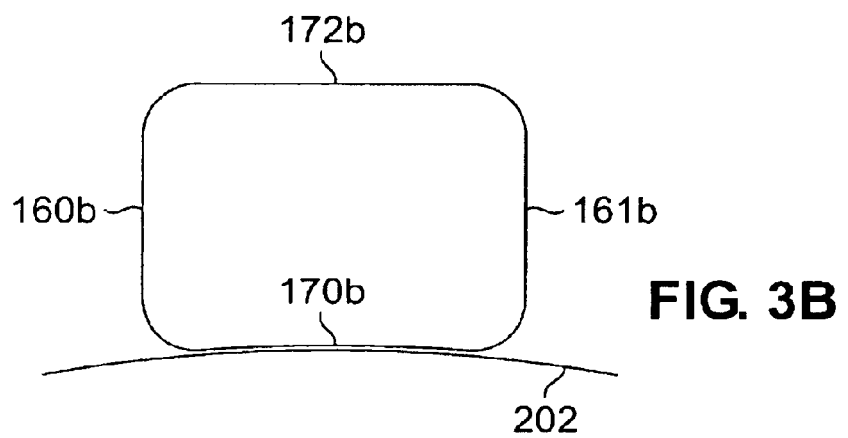
Figure 3C:
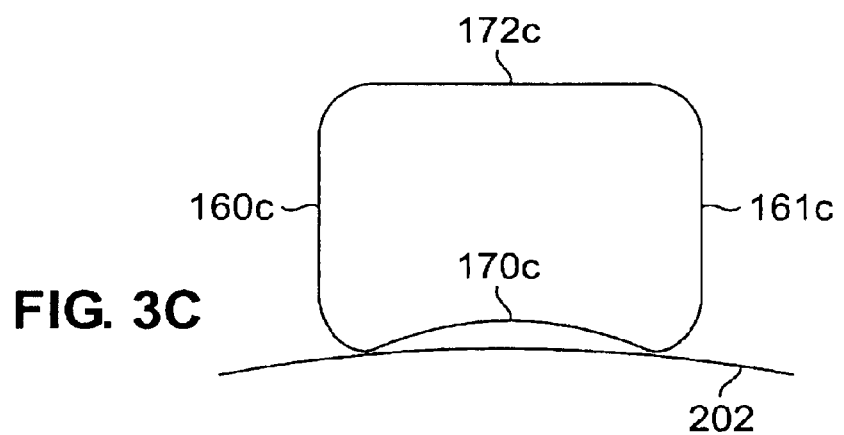

In the embodiment depicted in FIG. 3A, the bottom and top surfaces 170a and 172a are both straight in a direction transverse to the long axis of the prosthesis, as are side surfaces 160a and 161a, In the embodiment of FIG. 3B, however, while the top surface 172b and side surfaces 160b and 161b are al straight in directions transverse to the long axis of the prosthesis, the bottom surface 170b is curved in a direction transverse to the long axis of the prosthesis. The curvature of the example shown is approximately equal to the curvature of the innermost surface 202 of the scleral tunnel into which the prosthesis is to be implanted. The bottom surface 170c in the embodiment of FIG. 3C is similarly curved in a direction transverse to the long axis of the prosthesis, but with a curvature greater than the curvature of the innermost surface 202 of the scleral tunnel. Top surface 172c and sides surfaces 160c and 161c are straight.

Figure 3D:
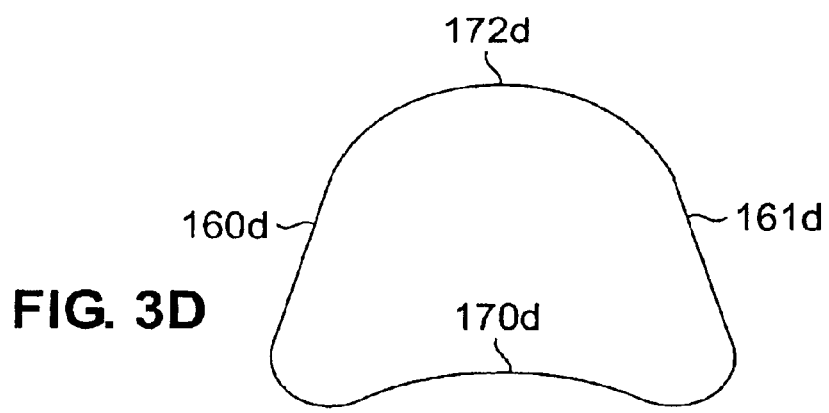

In the embodiment of FIG. 3D, the side surfaces 160d and 161d, while straight, are angled with respect to each other rather than being substantially parallel. Top surface 172d has a convex curvature in a direction transverse to the long axis of the prosthesis, and bottom surface 170d has a concave curvature.

Figure 3E:
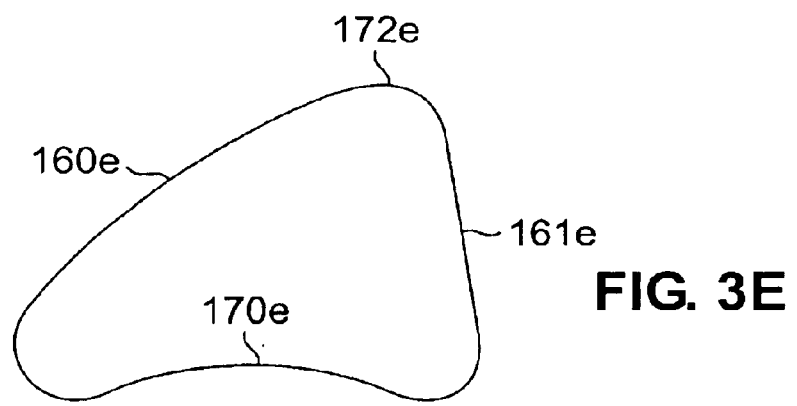

While the side surfaces 160d and 161d are uniformly or equally sloped in the embodiment of FIG. 3D, the side surfaces may be unequally sloped as shown in FIG. 3E to form an oblique profile. Side surfaces 160e and 161e are straight, and sloped to different degrees, while top surface 172e has a convex curvature and bottom surface 170e has a concave curvature.

Either or both of the side surfaces may alternatively be curved, either convexly or concavely, in a direction transverse to the long axis of the prosthesis, regardless of whether the side surfaces are substantially parallel to each other or angled with respect to each other. Moreover, the top surface may have a concave curvature, or the bottom surface may have a convex curvature.

While reference is made to side surfaces 160 and 161 and top and bottom surfaces 172 and 170 with respect to FIGS. 3A–3E, the profiles and/or curvatures illustrated are equally applicable to sides surfaces 162–165 or bottom surface 171. For example, while bottom surface 171 depicted in FIG. 1I is straight along a long axis of the prosthesis, the same surface may be curved in a direction transverse to the long axis in the manner illustrated in FIGS. 3B-3C.

FIGS. 4A through 4D are transverse cross-sectional views of duck bill end portions of a prosthesis for increasing the effective working distance of the ciliary muscle by implantation into surgically formed scleral pockets or tunnels according to various alternative embodiments of the present invention. FIGS. 4A through 4D depict a cross-section taken along section lines C—C, transverse to a long axis of the prosthesis, with the remainder of the prosthesis broken away. The end portion cross-sections depicted in FIGS. 4A through 4D may correspond to any of end portions 102, 103, 104, 106 or 107 depicted in FIGS. 1A–1J.

Figure 4A:
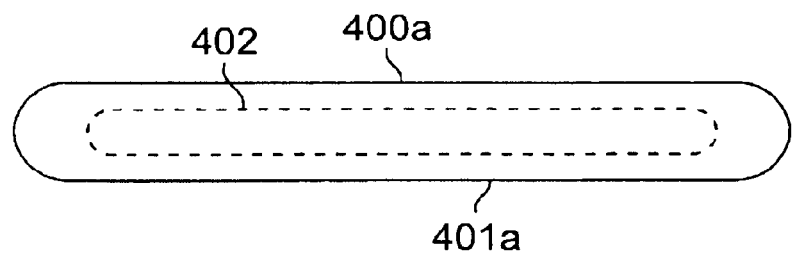
FIGS. 4A through 4D are transverse cross-sectional views of duck bill end portions of a prosthesis for increasing the effective working distance of the ciliary muscle by implantation into surgically formed scleral pockets or tunnels according to various alternative embodiments of the present invention.

In the embodiment of FIG. 4A, the top and bottom surfaces 400a and 401a of the end portion are straight in a direction transverse to the long axis of the prosthesis. Comparison of FIG. 3A with FIG. 4A shows that the prosthesis (which may be prosthesis 100, 110, 130, 140, 150 or 160) has a cross-section within the end portions which is wider and thinner than the cross-section of the central body portion. However, the cross-sectional circumference and/or area of the end portions should preferably not be significantly greater than the cross-sectional circumference and/or area of the central body portion. In this manner, the end portion may pass through an incision forming an opening to a scleral tunnel intended to accommodate the central body portion without tearing. The size of the surgical incision required to form a scleral tunnel which will admit the central body portion of the prosthesis without tearing (i.e., an incision having a length which is at least twice the circumference of the cross-section of the central body portion) will also permit passage of the end portion therethrough without tearing.

Most preferably, the cross-sectional circumference and/or area of the end portion intended to pass through the scleral tunnel should be equal to or less than the cross-sectional circumference and/or area of the corresponding central body portion. For this reason, an embodiment such as that illustrated in FIGS. 1C–1D, in which one duck bill end portion is narrower and/or thinner than the other, may be beneficially employed. Dashed outline 402 illustrates a relative proportion for the differently sized duck bill end portions.

Figure 4B:
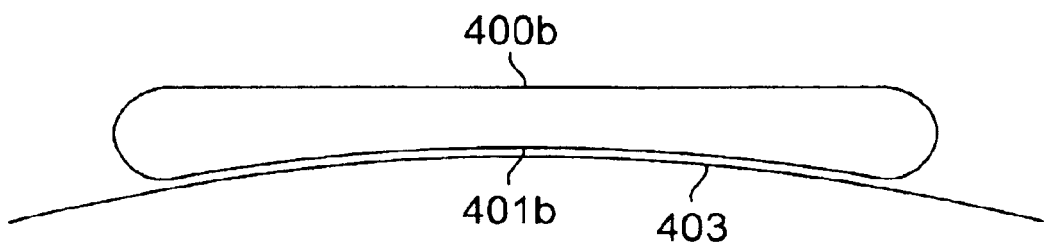

FIG. 4B illustrates an embodiment including a top surface 400b which is straight but a bottom surface 401b which is curved along a direction transverse to the long axis of the prosthesis. The curvature of the bottom surface 401b in the example of FIG. 4B is approximately equal to the curvature of the scleral surface 403 upon which the respective end portion is intended to rest following implantation of the prosthesis.

Figure 4C:
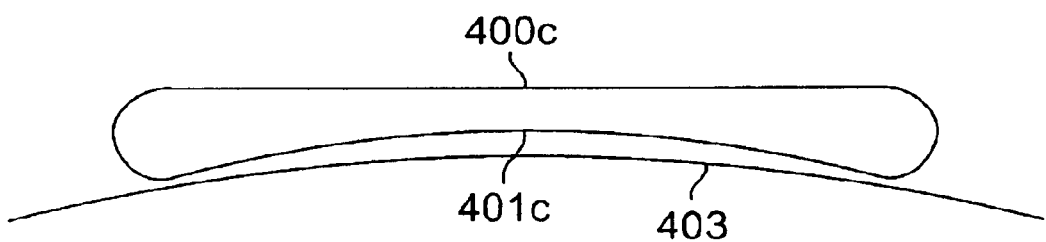

FIG. 4C similarly illustrates an embodiment including a top surface 400c which is straight but a bottom surface 401c which is curved along a direction transverse to the long axis of the prosthesis. However, the curvature of the bottom surface 401c in FIG. 4C is greater than the curvature of the sclera surface 403 upon which the respective end portion is intended to rest following implantation of the prosthesis. In this manner, the force of contact between the duck bill end portions and the underlying sclera occurs near the edge of the respective end portion, maximizing the effect of the end portion in preventing rotation of the implanted prosthesis.

Figure 4D:
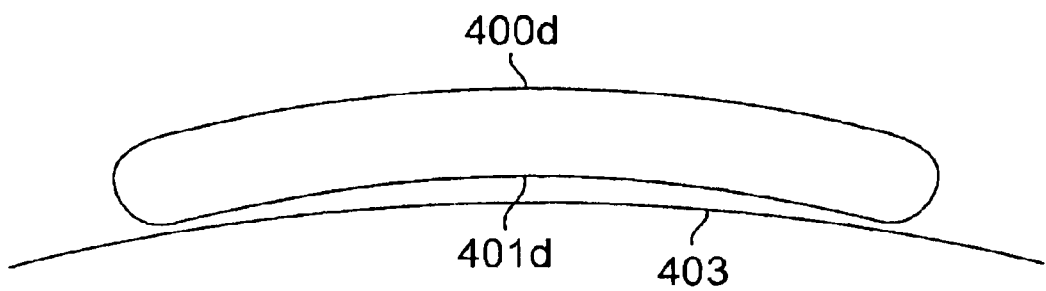

FIG. 4D illustrates an embodiment in which both the top surface 400d and the bottom surface 401d which is curved along a direction transverse to the long axis of the prosthesis.

Figure 5A:
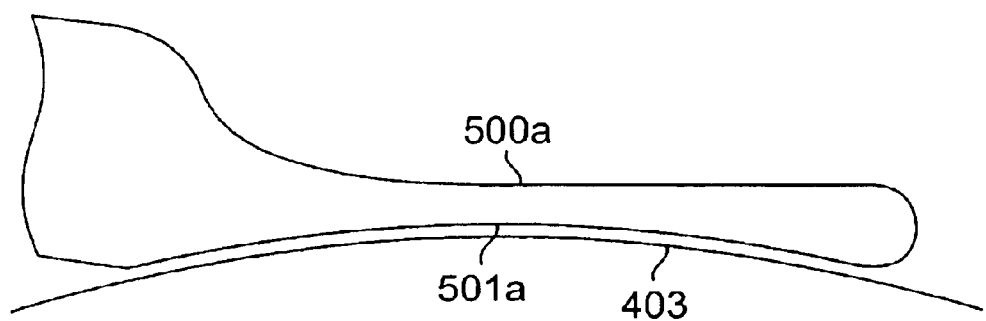
FIGS. 5A and 5B are longitudinal cross-sections of duck bill end portions of a prosthesis for increasing the effective working distance of the ciliary muscle by implantation into surgically formed scleral pockets or tunnels according to various alternative embodiments of the present invention.
Figure 5B:
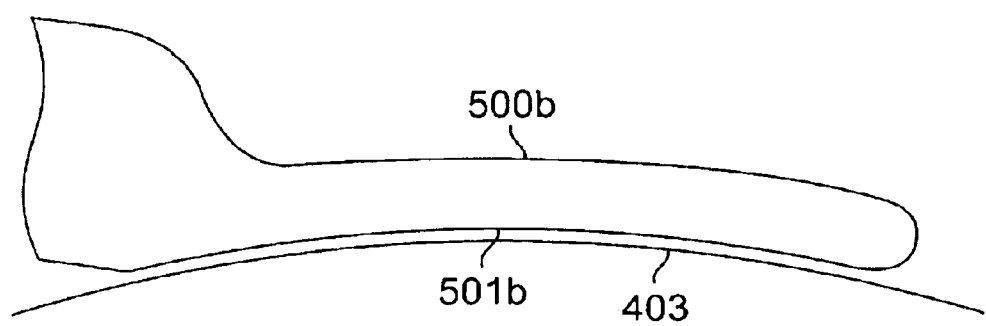

FIGS. 5A and 5B are longitudinal cross-sectional views of duck bill end portions of a prosthesis for increasing the effective working distance of the ciliary muscle by implantation into surgically formed scleral pockets or tunnels according to various alternative embodiments of the present invention. FIGS. 5A and 5D depict a cross-section of an end portion taken along section lines A—A with the remainder of the prosthesis broken away. The end portion cross-sections depicted in FIGS. 5A and 5B may correspond to any of end portions 102, 103, 104, 106 or 107 depicted in FIGS. 1A–1J.

FIG. 5A depicts an embodiment in which the top surface 500a is straight but the bottom surface 501a of a duck bill end portion is curved along the long axis of the prosthesis, at least in a central area of the end portion (i.e., the cross-section may be straight near an edge of the end portion). The curvature of the bottom surface 501a in the example of FIG. 5A is approximately equal to the curvature of the scleral surface 403 upon which the respective end portion is intended to rest following implantation of the prosthesis.

FIG. 5B depicts an embodiment in which both the top surface 500b and the bottom surface 501a of a duck bill end portion are curved along the long axis of the prosthesis, at least in a central area of the end portion.

Figure 6:
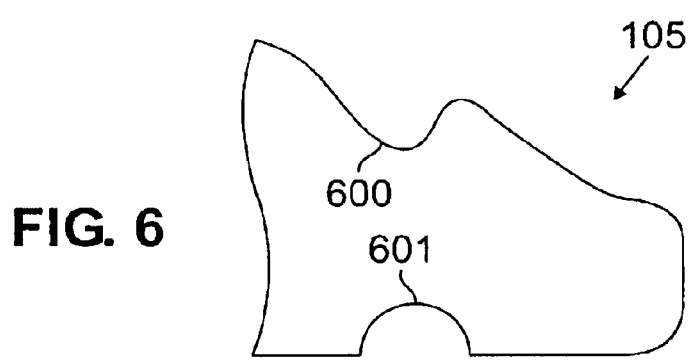
FIG. 6 is a longitudinal cross-section of a blunted end portion of a prosthesis for increasing the effective working distance of the ciliary muscle by implantation into surgically formed scleral pockets or tunnels according to one embodiment of the present invention.

FIG. 6 is a longitudinal cross-section of a blunted end portion of a prosthesis for increasing the effective working distance of the ciliary muscle by implantation into surgically formed scleral pockets or tunnels according to one embodiment of the present invention. Blunted end portion 105 includes one or more grooves 600 or 601, in the bottom surface, the top surface or both. Although not shown in FIG. 1F, grooves 600 and 601, if present, preferably extend across an entire width of the end portion 105. Grooves may be uniform, similar to groove 601, or oblique, similar to groove 600, and are intended to "catch" the lip of a scleral incision through which the prosthesis is inserted to inhibit sliding of the prosthesis within the scleral tunnel.

The dimensions of the central body portion of the prosthesis of the present invention are similar to the overall prosthesis dimension (including lengths, widths, thickness, and radii of curvature/heights for various curved surfaces) given in the related applications identified above. The prosthesis of the present invention may be fabricated of the same materials, and in the same manner, as those described in the related applications. Additionally, in treatment of eye disorders utilizing the prosthesis of the present invention, a number of prostheses are implanted in a single eye in the same manner as described in the related applications.

The present invention has been described in detail. Those skilled in the art will understand that various changes, substitutions and alterations may be made herein without departing from the spirit and scope of the invention in its broadest form.

What is claimed is:

1. A prosthesis adapted for contact with the sclera of an eyeball, said prosthesis comprising:
    a central body portion having a first end and a second end,
        at least one end portion extending from either said first or second end of said central body portion, said at least one end portion having a width greater than said central body portion,
    said central body portion having a bottom surface which is curved along a long axis of said prosthesis,
    wherein a curvature of said bottom surface is greater than a curvature of an innermost surface of a scleral pocket or tunnel into which said prosthesis is to be implanted,
    wherein said prosthesis is adapted to expand a portion of a sclera proximate to the scleral pocket or tunnel when said prosthesis is inserted within said scleral pocket or tunnel, and
    wherein said end portion is adapted to rest on a portion of said sclera outside said scleral pocket or tunnel when said prosthesis is inserted within said scleral pocket or tunnel and to inhibit rotation of said prosthesis within said scleral pocket or tunnel.

2. The prosthesis according to claim 1, wherein said at least one end portion has a width greater than a width of said scleral pocket or tunnel into which said prosthesis is to be implanted.

3. The prosthesis according to claim 1, wherein said prosthesis tapers steeply from a thickness of said central body portion to a thickness of said at least one end portion within a region where said at least one end portion joins said central body portion.

4. The prosthesis according to claim 1, wherein said at least one end portion has a flat bottom surface.

5. The prosthesis according to claim 1, wherein said prosthesis has an overall arcuate shape.

6. The prosthesis according to claim 1, further comprising:
    a tapered end portion extending from one of said first or second ends opposite another of said first and second ends from which said at least one end portion extends.

7. The prosthesis according to claim 1, further comprising:
    at least one groove within a surface of an end portion extending from one of said first or second ends opposite another of said first and second ends from which said at least one end portion extends.

* * * * *